US012426937B2

(12) United States Patent
Canady et al.

(10) Patent No.: US 12,426,937 B2
(45) Date of Patent: Sep. 30, 2025

(54) SYSTEM AND METHOD FOR SUPPRESSING APOE GENE FOR SARCOMA TREATMENT

(71) Applicant: Jerome Canady Research Institute for Advanced Biological and Technological Sciences, Takoma Park, MD (US)

(72) Inventors: Jerome Canady, Lakeland, FL (US); Lawan Ly, Annadale, FL (US); Saravana R K Murthy, Owings, MD (US); Xiaoqian Cheng, Fairfax, VA (US); Taisen Zhuang, Rockville, MD (US)

(73) Assignee: Jerome Canady Research Institute for Advanced Biological and Technological Sciences, Takoma Park, MD (US)

( * ) Notice: Subject to any disclaimer, the term of this patent is extended or adjusted under 35 U.S.C. 154(b) by 959 days.

(21) Appl. No.: 17/486,086

(22) Filed: Sep. 27, 2021

(65) Prior Publication Data

US 2022/0096140 A1    Mar. 31, 2022

Related U.S. Application Data

(60) Provisional application No. 63/083,621, filed on Sep. 25, 2020.

(51) Int. Cl.
*A61B 5/15* (2006.01)
*A61B 5/00* (2006.01)
(Continued)

(52) U.S. Cl.
CPC ........ *A61B 18/1206* (2013.01); *A61B 5/7435* (2013.01); *A61B 5/748* (2013.01);
(Continued)

(58) Field of Classification Search
CPC ... A61B 18/1206; A61B 5/7435; A61B 5/748; A61B 5/0033; A61B 5/0082;
(Continued)

(56) References Cited

U.S. PATENT DOCUMENTS 9,999,462 B2   6/2018  Canady et al.
10,023,858 B2  7/2018  Canady et al.
(Continued)

FOREIGN PATENT DOCUMENTS

TW    202122582 A  *  6/2021  ........... C07K 14/195
WO    2019/199281 A1   10/2019

OTHER PUBLICATIONS

Ren L, Yi J, Li W, et al. Apolipoproteins and cancer. Cancer Med. 2019; 8: 7032-7043. (Year: 2019).*

(Continued)

*Primary Examiner* — Kaitlyn E Smith
*Assistant Examiner* — Ana Veruska Guerrero
(74) *Attorney, Agent, or Firm* — 24IP Law Group USA, PLLC; Timothy R. DeWitt

(57) ABSTRACT

A method for applying cold atmospheric plasma treatment to target tissue comprising the steps of treating a patient with a pharmaceutical for suppressing apolipoprotein E genes, selecting through a graphical user interface a particular soft tissue sarcoma cell line associated with target tissue, retrieving, with the computing device, settings data associated with the selected soft tissue sarcoma cell line from a database of cell line data and associated settings data in a storage, and applying, with the computing device, the retrieved settings data to a cold atmospheric plasma system.

5 Claims, 19 Drawing Sheets

(51) Int. Cl.
*A61B 18/12* (2006.01)
*A61B 18/00* (2006.01)
*A61B 18/02* (2006.01)
*A61B 18/14* (2006.01)

(52) U.S. Cl.
CPC ........... *A61B 5/0033* (2013.01); *A61B 5/0082* (2013.01); *A61B 5/150335* (2013.01); *A61B 2018/00005* (2013.01); *A61B 2018/00077* (2013.01); *A61B 2018/00583* (2013.01); *A61B 2018/00636* (2013.01); *A61B 2018/00642* (2013.01); *A61B 2018/00779* (2013.01); *A61B 2018/00964* (2013.01); *A61B 2018/00988* (2013.01); *A61B 18/02* (2013.01); *A61B 18/1402* (2013.01); *A61B 2560/0204* (2013.01); *A61B 2560/0214* (2013.01); *A61B 2562/0247* (2013.01)

(58) Field of Classification Search
CPC .............. A61B 5/150335; A61B 18/02; A61B 18/1402; A61B 2018/00005; A61B 2018/00077; A61B 2018/00583; A61B 2018/00636; A61B 2018/00642; A61B 2018/00779; A61B 2018/00964; A61B 2018/00988; A61B 2560/0204; A61B 2560/0214; A61B 2562/0247; A61B 5/0071; A61B 2018/00732; A61B 2090/064; A61B 18/042

See application file for complete search history.

(56) References Cited

U.S. PATENT DOCUMENTS

| | | | |
|---|---|---|---|
| 10,213,614 | B2 | 2/2019 | Keidar et al. |
| 10,405,913 | B2 | 9/2019 | Canady et al. |
| 10,973,564 | B2 * | 4/2021 | Canady ..................... H05H 1/46 |
| 10,980,591 | B2 | 4/2021 | Canady et al. |
| 11,020,545 | B2 | 6/2021 | Canady et al. |
| 2011/0212090 | A1 * | 9/2011 | Pedersen ................. A61P 35/00 424/234.1 |
| 2014/0171854 | A1 * | 6/2014 | Jacofsky .................. A61N 1/44 604/23 |
| 2014/0378892 | A1 | 12/2014 | Guron et al. |
| 2016/0138006 | A1 * | 5/2016 | Canady ................ A61B 18/042 606/34 |
| 2017/0183631 | A1 * | 6/2017 | Keidar .................... H05H 1/245 |
| 2018/0117249 | A1 * | 5/2018 | Pennington ........ A61B 5/14532 |
| 2020/0237422 | A1 | 7/2020 | Canady et al. |
| 2020/0261140 | A1 | 8/2020 | Canady et al. |
| 2020/0384278 | A1 | 12/2020 | Canady et al. |
| 2021/0015537 | A1 | 1/2021 | Canady et al. |

OTHER PUBLICATIONS

A. Fridman, Plasma Chemistry (Cambridge University Press, 2008).
E. Stoffels, Y. Sakiyama, and D.B. Graves "Cold Atmospheric Plasma: Charged Species and Their Interactions With Cells and Tissues" IEEE Trans. Plasma Sci. 36, 1441 (2008).
X. Lu, Y. Cao, P. Yang, Q. Xiong, Z. Xiong, Y. Xian, and Y. Pan "An RC Plasma Device for Sterilization of Root Canal of Teeth" IEEE Trans. Plasma Sci. 37, 668 (2009).
K.H. Becker, K.H. Shoenbach and J.G. Eden "Microplasma and applications" J. Phys. D.: Appl. Phys. 39, R55-R70 (2006).
E. Stoffels, I.E Kieft, R.E.J Sladek, L.J.M van den Bedem, E.P van der Laan, M. Steinbuch "Plasma needle for in vivo medical treatment: recent developments and perspectives" Plasma Sources Sci. Technol. 15, S169-S180 (2006).
Yan D, Sherman J H and Keidar M, "Cold atmospheric plasma, a novel promising anti-cancer treatment modality," Oncotarget. 8 15977-15995 (2017).
Keidar M, "Plasma for cancer treatment," Plasma Sources Sci. Technol. 24 33001 (2015).
Hirst A M, Frame F M, Arya M, Maitland N J and O'Connell D, "Low temperature plasmas as emerging cancer therapeutics: the state of play and thoughts for the future," Tumor Biol. 37 7021-7031 (2016).
Keidar M, Walk R, Shashurin A, Srinivasan P, Sandler A, Dasgupta S, Ravi R, Guerrero-Preston R and Trink B, "Cold plasma selectivity and the possibility of a paradigm shift in cancer therapy," Br. J. Cancer. 105 1295-301 (2011).
Vandamme M, Robert E, Dozias S, Sobilo J, Lerondel S, Le Pape A and Pouvesle J-M, "Response of human glioma U87 xenografted on mice to non thermal plasma treatment," Plasma Med. 1 27-43 (2011).
Brulle L, Vandamme M, Ries D, Martel E, Robert E, Lerondel S, Trichet V, Richard S, Pouvesle J M and Le Pape A, "Effects of a Non thermal plasma treatment alone or in combination with gemcitabine in a MIA PaCa2-luc orthotopic pancreatic carcinoma model," PLoS One. 7 e52653 (2012).
Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," Plasma Process. Polym. 12 1400-1409 (2015).
Ahn H J, Kim K Il, Kim G, Moon E, Yang S S and Lee J S, "Atmospheric-pressure plasma jet induces apoptosis involving mitochondria via generation of free radicals,". PLoS One. 6 e28154 (2011).
Ja Kim S, Min Joh H and Chung T H, "Atmospheric-pressure plasma jet induces apoptosis and change of cell viability induced by atmospheric pressure plasma in normal and cancer cells," Appl. Phys. Lett. 103 153705 (2013).
Yan D, Talbot A, Nourmohammadi N, Sherman J H, Cheng X and Keidar M, "Toward understanding the selective anticancer capacity of cold atmospheric plasma—a model based on aquaporins (Review)," Biointerphases. 10 040801 (2015).
Yan D, Xiao H, Zhu W, Nourmohammadi N, Zhang L G, Bian K and Keidar M, "The role of aquaporins in the anti-glioblastoma capacity of the cold plasma-stimulated medium," J. Phys. D. Appl. Phys. 50 055401 (2017).
Yan D, Talbot A, Nourmohammadi N, Cheng X, Canady J, Sherman J and Keidar M, "Principles of using cold atmospheric plasma stimulated media for cancer treatment," Sci. Rep. 5 18339 (2015).
Ma Y, Ha C S, Hwang S W, Lee H J, Kim G C, Lee K W and Song K, "Non-thermal atmospheric pressure plasma preferentially induces apoptosis in p53-mutated cancer cells by activating ROS stress-response pathways," PLoS One. 9 e91947 (2014).
Sablina A A, Budanov A V, Ilyinskaya G V, Larissa S, Kravchenko J E and Chumakov P M, "The antioxidant function of the p53 tumor suppressor," Nat. Med. 11 1306 (2005).
Maillet A and Pervaiz S, "Redox regulation of p53, redox effectors regulated by p53: a subtle balance," Antioxid. Redox Signal. 16 1285-1294 (2012).
Naciri M, Dowling D and Al-Rubeai M, "Differential sensitivity of mammalian cell lines to non-thermal atmospheric plasma," Plasma Process. Polym. 11 391-400 (2014).
Fearon E F and Vogelstein B, "A genetic model for colorectal tumorigenesis," Cell. 61 759-767 (1990).
Yan D, Cui H, Zhu W, Nourmohammadi N, Milberg J, Zhang L G, Sherman J H and Keidar M, "The specific vulnerabilities of cancer cells to the cold atmospheric plasma-stimulated solutions," Sci. Rep. 7 4479 (2017).
G.Fridman, G. Friedman, A. Gutsol, A. B. Shekhter, V. N. Vasilets, and A. Fridman "Applied Plasma Medicine", Plasma Processes Polym. 5, 503 (2008).

\* cited by examiner

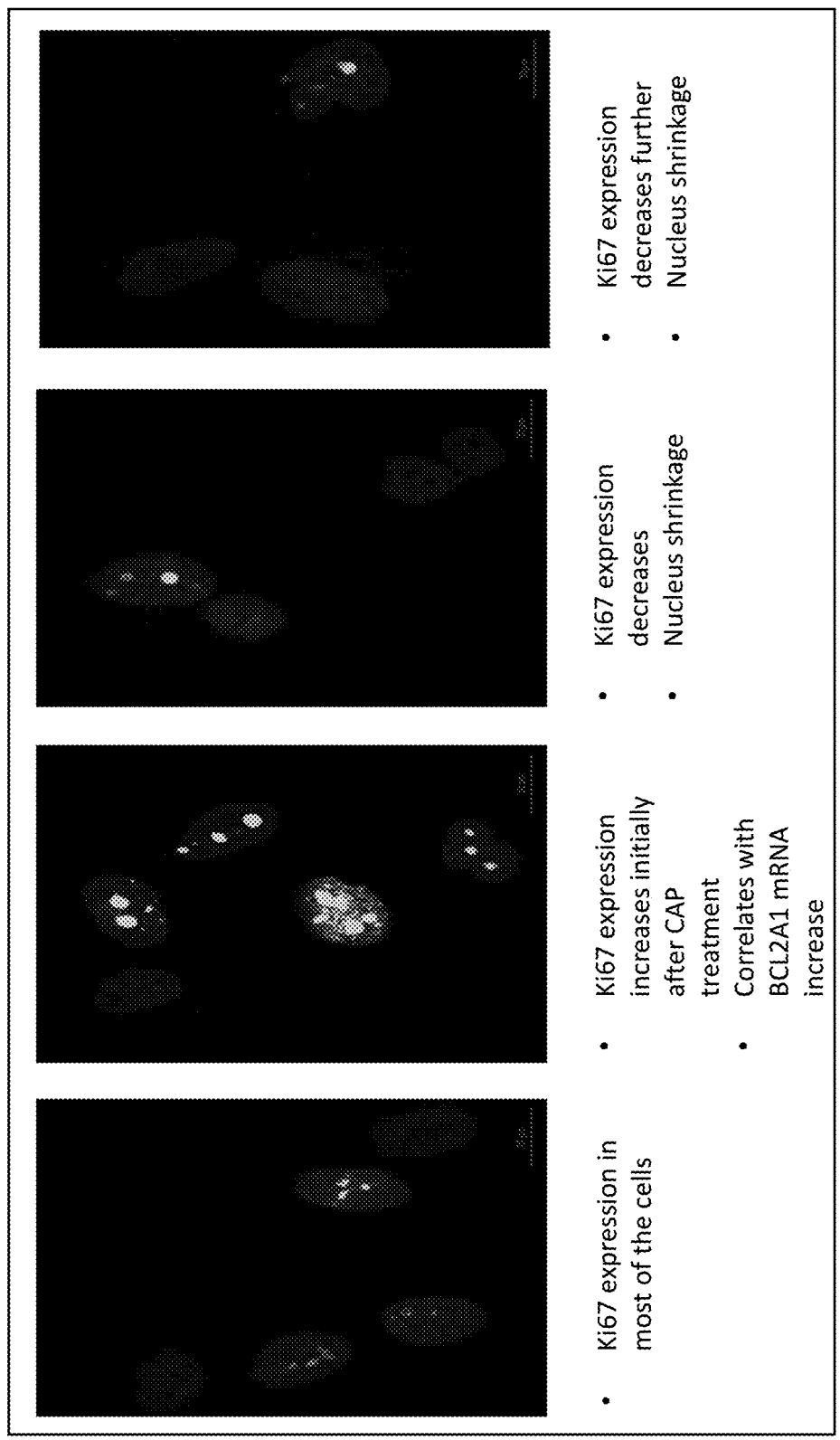

| | 0 hr | 6 hr | 12 hr | 24 hr | 36 hr | 48 hr |
|---|---|---|---|---|---|---|
| No Treatment | Cells evenly distributed and proliferating in G1, S, G2, and M phase | | | | | |
| 120 P 5min | Cells arrested in S/G2/M | Cells arrested in S/G2/M | Cells arrested in S/G2/M | Cells begin to recover | More cells in G1 | Cells have recovered and divided |
| 120 P 7min | Cells arrested in S/G2/M | Cells arrested in S/G2/M | Cells begin to shrink | Apoptosis initiated | Dead cells | Cell debris |

FIG. 3

SYSTEM AND METHOD FOR SUPPRESSING APOE GENE FOR SARCOMA TREATMENT

CROSS-REFERENCE TO RELATED APPLICATIONS

The present application claims the benefit of the filing date of U.S. Provisional Patent Application Ser. No. 63/083,621 filed by the present inventors on Sep. 25, 2020.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for treating soft tissue sarcoma with cold atmospheric plasma.

Brief Description of the Related Art

Soft tissue sarcoma is a malignant tumor that most often develops in adults but can occur in children as well. Treatment with radiation, en bloc surgical resection and chemotherapy have achieved long-term survival rates up to 65% to 80% in non-metastatic disease. Local microscopic tumor cells can still exist despite complete R-0 surgical excision of the tumor.

The unique chemical and physical properties of cold atmospheric plasmas enable their numerous recent applications in biomedicine including sterilization, the preparation of polymer materials for medical procedures, wound healing, tissue or cellular removal and dental drills. A. Fridman, Plasma Chemistry (Cambridge University Press, 2008); G. Fridman, G. Friedman, A. Gutsol, A. B. Shekhter, V. N. Vasilets, and A. Fridman "Applied Plasma Medicine", Plasma Processes Polym. 5, 503 (2008); E. Stoffels, Y. Sakiyama, and D. B. Graves "Cold Atmospheric Plasma: Charged Species and Their Interactions With Cells and Tissues" IEEE Trans. Plasma Sci. 36, 1441 (2008); X. Lu, Y. Cao, P. Yang, Q. Xiong, Z. Xiong, Y. Xian, and Y. Pan "An RC Plasma Device for Sterilization of Root Canal of Teeth" IEEE Trans. Plasma Sci. 37, 668 (2009).

Plasma-based nitrogen oxide (NO) therapy demonstrated huge potential for stimulation of regenerative processes and wound healing. The work uncovering function of nitrogen oxide as a signal molecule was awarded by the Nobel Prize in medicine and biology in 1999. NO-therapy demonstrated tremendous effect of acceleration of healing of ulcer, burns and serious wounds. Other experimental evidence supports efficiency of cold plasmas produced by dielectric barrier discharge for apoptosis of melanoma cancer cell lines, treatment of cutaneous leishmaniasis, ulcerous eyelid wounds, corneal infections, sterilization of dental cavities, skin regeneration, etc.

Recent progress in atmospheric plasmas led to creation of cold plasmas with ion temperatures close to room temperature. Cold non-thermal atmospheric plasmas can have tremendous applications in biomedical technology. K. H. Becker, K. H. Shoenbach and J. G. Eden "Microplasma and applications" J. Phys. D.: Appl. Phys. 39, R55-R70 (2006). In particular, plasma treatment can potentially offer a minimum-invasive surgery that allows specific cell removal without influencing the whole tissue. Conventional laser surgery is based on thermal interaction and leads to accidental cell death i.e., necrosis and may cause permanent tissue damage. In contrast, non-thermal plasma interaction with tissue may allow specific cell removal without necrosis. In particular, these interactions include cell detachment without affecting cell viability, controllable cell death etc. It can be used also for cosmetic methods of regenerating the reticular architecture of the dermis. The aim of plasma interaction with tissue is not to denaturate the tissue but rather to operate under the threshold of thermal damage and to induce chemically specific response or modification. In particular presence of the plasma can promote chemical reaction that would have desired effect. Chemical reaction can be promoted by tuning the pressure, gas composition and energy. Thus, the important issues are to find conditions that produce effect on tissue without thermal treatment. Overall plasma treatment offers the advantage that is can never be thought of in most advanced laser surgery. E. Stoffels, I. E Kieft, R. E. J Sladek, L. J. M van den Bedem, E. P van der Laan, M. Steinbuch "Plasma needle for in vivo medical treatment: recent developments and perspectives" Plasma Sources Sci. Technol. 15, S169-S180 (2006).

Several different systems and methods for performing Cold Atmospheric Plasma (CAP) treatment have been disclosed. For example, U.S. Published Patent Application No. 2014/0378892 discloses a two-electrode system for CAP treatment. U.S. Pat. No. 9,999,462 discloses a converter unit for using a traditional electrosurgical system with a single electrode CAP accessory to perform CAP treatment.

As a near-room temperature ionized gas, cold atmospheric plasma (CAP) has demonstrated its promising capability in cancer treatment by causing the selective death of cancer cells in vitro. See, Yan D, Sherman J H and Keidar M, "Cold atmospheric plasma, a novel promising anti-cancer treatment modality," Oncotarget. 8 15977-15995 (2017); Keidar M, "Plasma for cancer treatment," Plasma Sources Sci. Technol. 24 33001 (2015); Hirst A M, Frame F M, Arya M, Maitland N J and O'Connell D, "Low temperature plasmas as emerging cancer therapeutics: the state of play and thoughts for the future," Tumor Biol. 37 7021-7031 (2016). The CAP treatment on several subcutaneous xenograft tumors and melanoma in mice has also demonstrated its potential clinical application. See, Keidar M, Walk R, Shashurin A, Srinivasan P, Sandler A, Dasgupta S, Ravi R, Guerrero-Preston R and Trink B, "Cold plasma selectivity and the possibility of a paradigm shift in cancer therapy," Br. J. Cancer. 105 1295-301 (2011); Vandamme M, Robert E, Dozias S, Sobilo J, Lerondel S, Le Pape A and Pouvesle J-M, "Response of human glioma U87 xenografted on mice to non thermal plasma treatment," Plasma Med. 1 27-43 (2011); Brulle L, Vandamme M, Ries D, Martel E, Robert E, Lerondel S, Trichet V, Richard S, Pouvesle J M and Le Pape A, "Effects of a Non thermal plasma treatment alone or in combination with gemcitabine in a MIA PaCa2-luc orthotopic pancreatic carcinoma model," PLoS One. 7 e52653 (2012); and Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," Plasma Process. Polym. 12 1400-1409 (2015).

The rise of intracellular reactive oxygen species (ROS), DNA damage, mitochondrial damage, as well as apoptosis have been extensively observed in the CAP-treated cancer cell lines. See, Ahn H J, Kim K Il, Kim G, Moon E, Yang S S and Lee J S, "Atmospheric-pressure plasma jet induces apoptosis involving mitochondria via generation of free radicals,". *PLoS One.* 6 e28154 (2011); Ja Kim S, Min Joh H and Chung T H, "Production of intracellular reactive oxygen species and change of cell viability induced by atmospheric pressure plasma in normal and cancer cells," *Appl. Phys. Lett.* 103 153705 (2013); and Yan D, Talbot A, Nourmohammadi N, Sherman J H, Cheng X and Keidar M, "Toward understanding the selective anticancer capacity of cold atmospheric plasma—a model based on aquaporins (Review)," *Biointerphases.* 10 040801 (2015). The increase of intracellular ROS may be due to the complicated intracellular pathways or the diffusion of extracellular ROS through the cellular membrane. See, Yan D, Xiao H, Zhu W, Nourmohammadi N, Zhang L G, Bian K and Keidar M, "The role of aquaporins in the anti-glioblastoma capacity of the cold plasma-stimulated medium," *J. Phys. D. Appl. Phys.* 50 055401 (2017). However, the exact underlying mechanism is still far from clear.

Cancer cells have shown specific vulnerabilities to CAP. See, Yan D, Talbot A, Nourmohammadi N, Cheng X, Canady J, Sherman J and Keidar M, "Principles of using cold atmospheric plasma stimulated media for cancer treatment," *Sci. Rep.* 5 18339 (2015)

Understanding the vulnerability of cancer cells to CAP will provide key guidelines for its application in cancer treatment. Only two general trends about the cancer cells' vulnerability to CAP treatment have been observed in vitro based on just a few cell lines. First, one study just compared the cytotoxicity of CAP treatment on the cancer cell lines expressing p53 with the same treatment on the cancer cell lines without expressing p53. The cancer cells expressing the p53 gene were shown to be more resistant to CAP treatment than p53 minus cancer cells. Ma Y, Ha C S, Hwang S W, Lee H J, Kim G C, Lee K W and Song K, "Non-thermal atmospheric pressure plasma preferentially induces apoptosis in p53-mutated cancer cells by activating ROS stress-response pathways," *PLoS One.* 9 e91947 (2014). p53, a key tumor suppressor gene, not only restricts abnormal cells via the induction of growth arrest or apoptosis, but also protects the genome from the oxidative damage of ROS such as $H_2O_2$ through regulating the intracellular redox state. Sablina A A, Budanov A V, Ilyinskaya G V, Larissa S, Kravchenko J E and Chumakov P M, "The antioxidant function of the p53 tumor suppressor," *Nat. Med.* 11 1306 (2005). p53 is an upstream regulator of the expression of many antioxidant enzymes such as glutathione peroxidase (GPX), glutaredoxin 3 (Grx3), and manganese superoxide dismutase (MnSOD). Maillet A and Pervaiz S, "Redox regulation of p53, redox effectors regulated by p53: a subtle balance," *Antioxid. Redox Signal.* 16 1285-1294 (2012). In addition, the cancer cells with a lower proliferation rate are more resistant to CAP than cancer cells with a higher proliferation rate. Naciri M, Dowling D and Al-Rubeai M, "Differential sensitivity of mammalian cell lines to non-thermal atmospheric plasma," *Plasma Process. Polym.* 11 391-400 (2014). This trend may be due to the general observation that the loss of p53 is a key step during tumorigenesis. Tumors at a high tumorigenic stage are more likely to have lost p53. See, Fearon E F and Vogelstein B, "A genetic model for colorectal tumorigenesis," *Cell.* 61 759-767 (1990).

Despite the complicated interaction between CAP and cancer cells, the initial several hours after treatment has been found to be an important stage for the cytotoxicity of CAP. The anti-cancer ROS molecules in the extracellular medium are completely consumed by cells during this time period. After the initial several hours, replacing the medium surrounding the cancer cells does not change the cytotoxicity of CAP. See, Yan D, Cui H, Zhu W, Nourmohammadi N, Milberg J, Zhang L G, Sherman J H and Keidar M, "The specific vulnerabilities of cancer cells to the cold atmospheric plasma-stimulated solutions," *Sci. Rep.* 7 4479 (2017).

SUMMARY OF THE INVENTION

Cold atmospheric plasma (CAP) reduces sarcoma cell viability in a time- and power-dependent manner. With optimal dosage for each cancer type, soft tissue sarcomas may be treated effectively.

In a preferred embodiment the present invention is a method for using cold atmospheric plasma to produce a pharmaceutical for suppressing apolipoprotein E genes in a cancer patient.

In another preferred embodiment the present invention is a pharmaceutical for suppressing apolipoprotein E genes in a cancer patient.

In still another embodiment, the present invention is a method for treating cancer. The method comprises treating a patient with a pharmaceutical for suppressing apolipoprotein E genes, surgically resecting a liposarcoma from the patient and performing cold atmospheric plasma treatment on the surgical margins of the area in the patient where the liposarcoma was resected. The method may further comprise performing intraoperative radiation treatment on the patient during the surgical resection of the liposarcoma from the patent. The cold atmospheric plasma treatment preferably is performed for at least 7 minutes at a power setting of 120P.

In another embodiment, the present invention is a method for applying cold atmospheric plasma treatment to target tissue comprising the steps of treating a patient with a pharmaceutical for suppressing apolipoprotein E genes, surgically resecting a liposarcoma from the patient, selecting through a graphical user interface a particular liposarcoma cell line associated with target tissue, retrieving, with said computing device, settings data associated with said selected liposarcoma cell line from a database of cell line data and associated settings data in a storage, applying, with said computing device, said retrieved settings data to a cold atmospheric plasma system, and performing cold atmospheric plasma treatment on the surgical margins of the area in the patient where the liposarcoma was resected.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 2A, 2B, 2C and 2D are images illustrating proliferation of 94T778 liposarcoma being reduced by CAP.

FIG. 3 is a series of images illustrating cell cycle arrest of liposarcoma by CAP Treatment.

DETAILED DESCRIPTION OF THE PREFERRED EMBODIMENTS

Cold atmospheric plasma (CAP) reduces sarcoma cell viability in a time- and power-dependent manner. With optimal dosage for each cancer type, soft tissue sarcomas may be treated effectively.

The cell cycle can be expressed as follows: G1, S/G2/M, G2-S. Experiments have shown that 94T778 liposarcoma cells are arrested in S/G2/M phase but recover and continue to proliferate 24 hours post-CAP. As shown in FIG. 3, which illustrates cell cycle arrest of liposarcoma by CAP Treatment, at CAP treatment of 120P 5 min, 94T778 liposarcoma cells are arrested in S/G2/M phase but recover and continue to proliferate 24 hours post-CAP. At CAP treatment of 120P 7 min, however, cells are arrested in S/G2/M phase but never recover from apoptosis. Cells shrink after 12 hours, become spherical by 24 hours, and are completely dead by 48 hours.

Figure 1A:
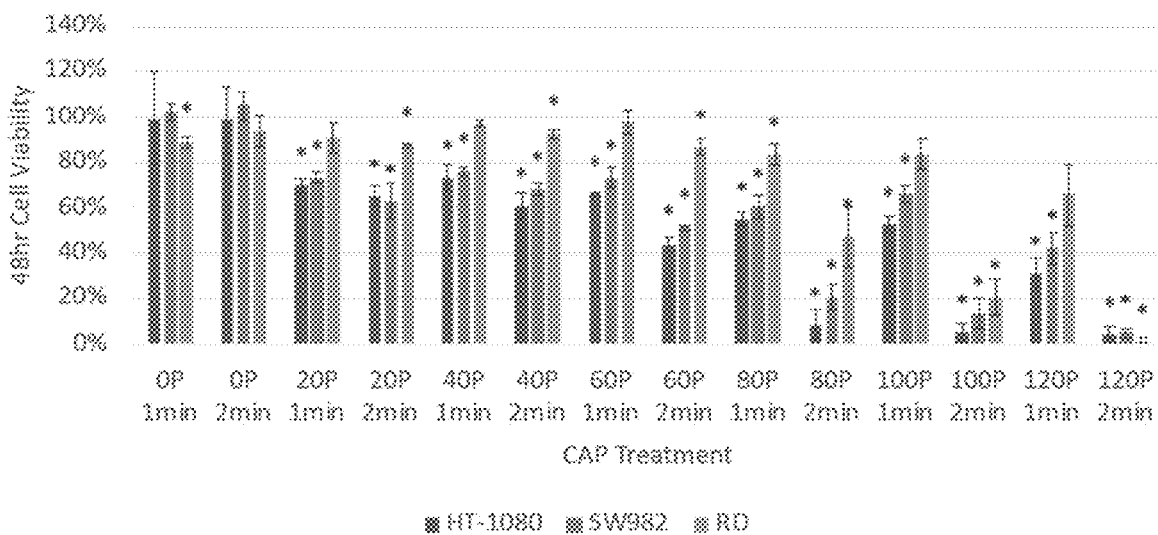
FIGS. 1A and 1B are graphs illustrating viability of HT-1080 connective tissue fibrosarcoma, SW982 synovial sarcoma, RD muscle rhabdomyosarcoma and 94T778 well-differentiate liposarcoma 48 hours post-CAP treatment is reduced significantly. (*p≤0.05).
Figure 1B:
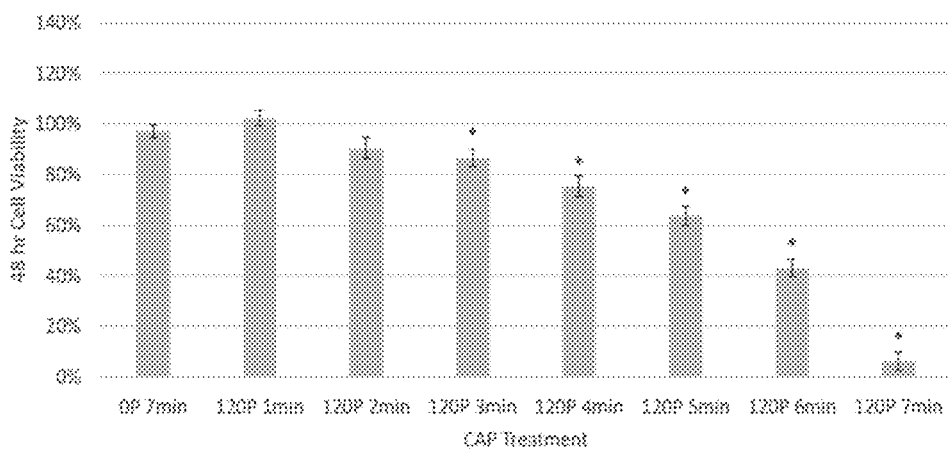

FIGS. 1A and 1B are graphs illustrating viability of HT-1080 connective tissue fibrosarcoma, SW982 synovial sarcoma, RD muscle rhabdomyosarcoma and 94T778 well-differentiate liposarcoma 48 hours post-CAP treatment reduced significantly. (*p≤0.05).

FIGS. 2A, 2B, 2C and 2D are images illustrating proliferation of 94T778 liposarcoma being reduced by CAP. The 94T778 (Liposarcoma) is treated at 120 W for 5 minutes. Ki67 (proliferative marker) DAPI (nucleus) co-staining Imaged by confocal microscope at 6 h, 24 h, 48 h post-CAP.

FIG. 3 is a series of images illustrating cell cycle arrest of liposarcoma by CAP Treatment.

Figure 4:
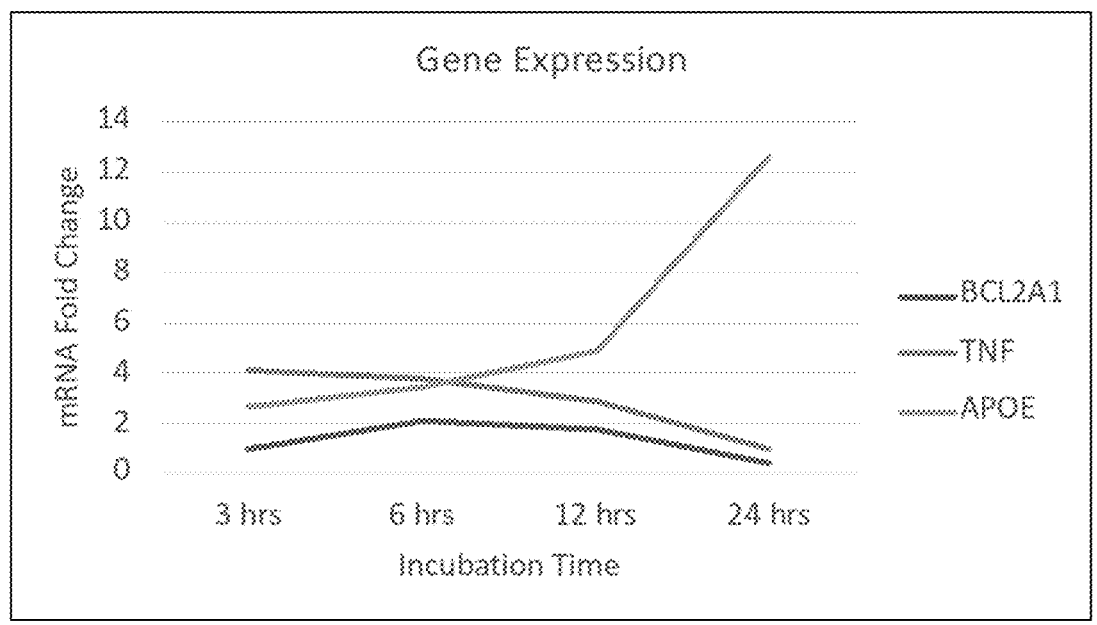
FIG. 4 is a graph illustrating the protective mechanism activation after CAP treatment.
Figure 5A:
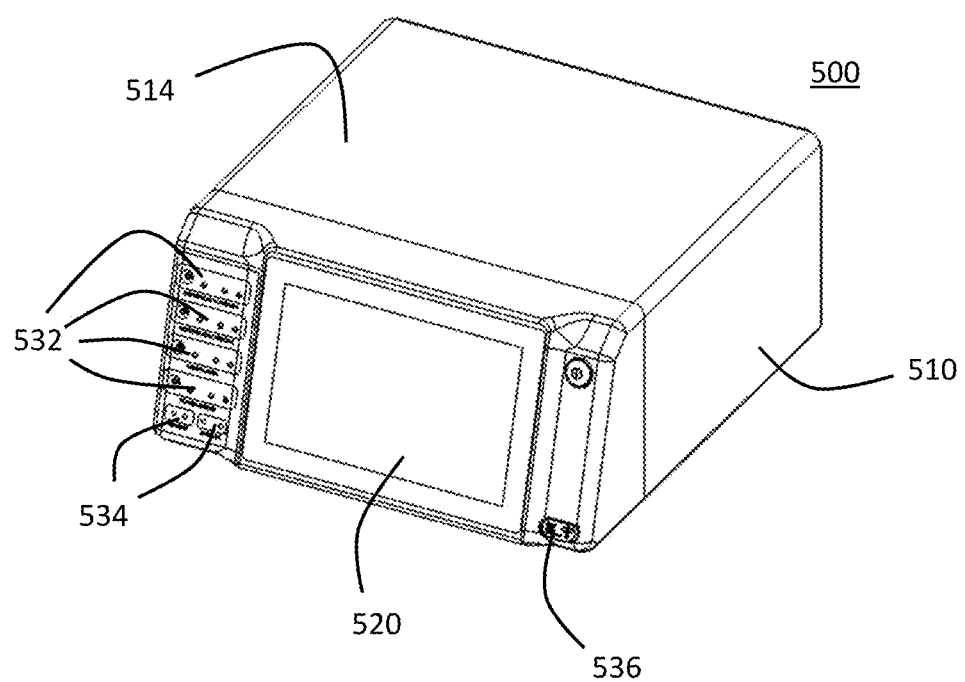
FIG. 5A is a perspective view of a preferred embodiment of a gas-enhanced electrosurgical generator.
Figure 5B:
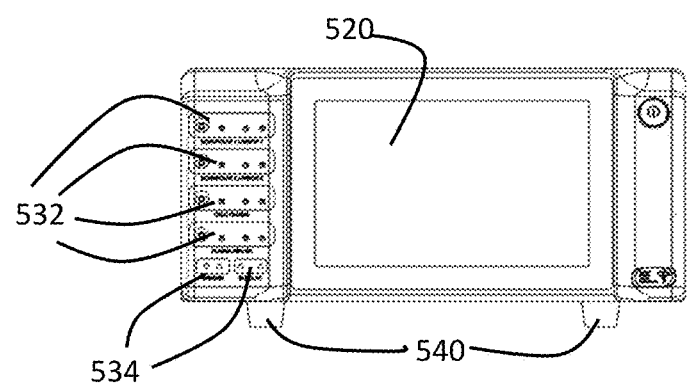
FIG. 5B is a front view of a preferred embodiment of a gas-enhanced electrosurgical generator.
Figure 5C:
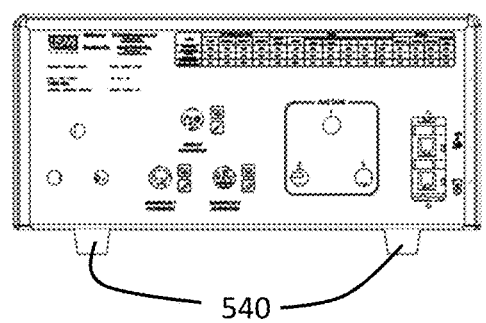
FIG. 5C is a rear view of a preferred embodiment of a gas-enhanced electrosurgical generator.
Figure 5D:
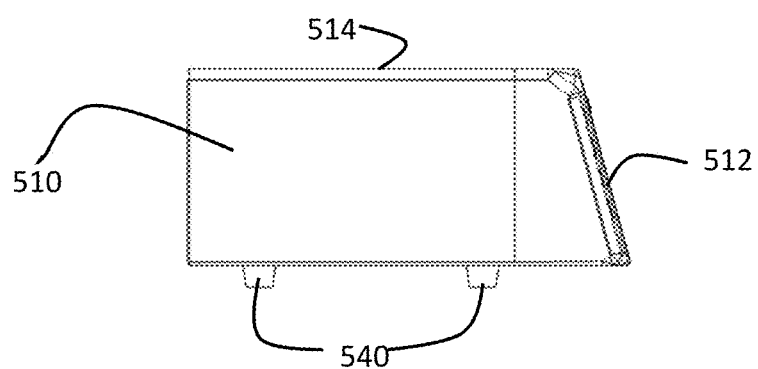
FIG. 5D is a left side view of a preferred embodiment of a gas-enhanced electrosurgical generator.
Figure 5E:
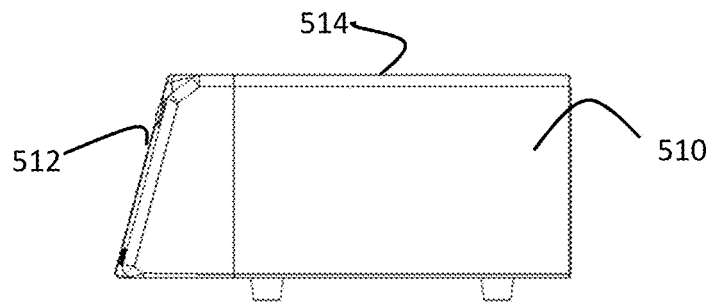
FIG. 5E is a right view of a preferred embodiment of a gas-enhanced electrosurgical generator.
Figure 5F:
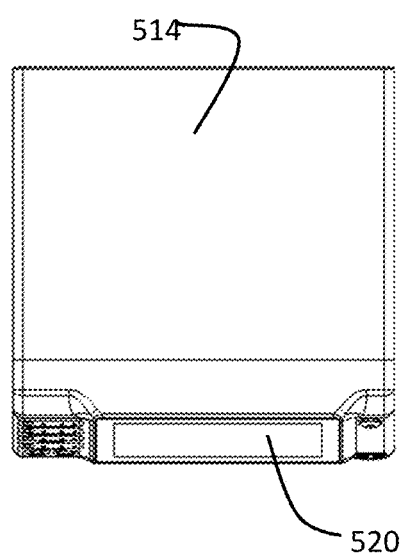
FIG. 5F is a top view of a preferred embodiment of a gas-enhanced electrosurgical generator.
Figure 5G:
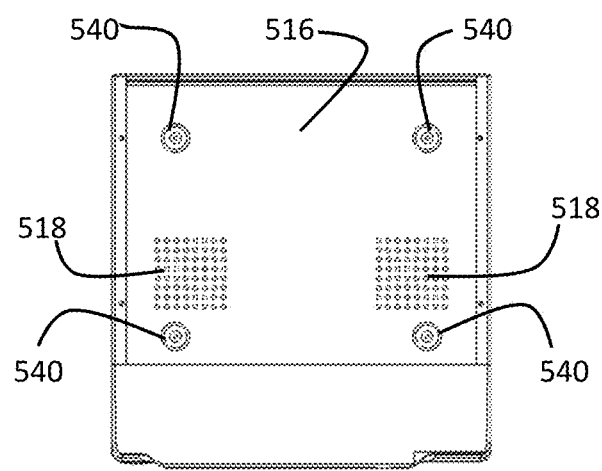
FIG. 5G is a bottom view of a preferred embodiment of a gas-enhanced electrosurgical generator.

FIG. 4 is a graph illustrating the protective mechanism activation after CAP treatment. Gene expression of 94T778 (Liposarcoma) cells: Anti-apoptotic genes, BCL2A1 and APOE (apolipoprotein E), and pro-apoptotic gene, TNF (tumor necrosis factor), mRNA levels were upregulated in 94T778 liposarcoma cells after CAP treatment at 120 P 5 min compared to mock controls. APOE mRNA expression levels peaked at 24 hours, suggesting that APOE acts as a defense mechanism against CAP-induced apoptosis in liposarcoma cells.

Based upon this, a pharmaceutical can be produced using CAP such that the pharmaceutical can suppress the APOE gene and thereby allow for more effective treatment of liposarcoma using CAP and other treatment modalities alone or in combination.

Cold plasmas for use in connection with the present invention and experiments described herein may be produced in a variety of ways, such as are shown in U.S. Pat. No. 10,973,564 entitled "Integrated Cold Plasma and High Frequency Plasma Electrosurgical System and Method."

A preferred embodiment of a CAP enabled generator is described with reference to the drawings. A gas-enhanced electrosurgical generator 500 in accordance with a preferred embodiment of the present invention is shown in FIGS. 5A-5G. The gas-enhanced generator has a housing 510 made of a sturdy material such as plastic or metal similar to materials used for housings of conventional electrosurgical generators. The housing 510 has a removable cover 514. The housing 510 and cover 514 have means, such as screws 519, tongue and groove, or other structure for removably securing the cover to the housing. The cover 514 may comprise just the top of the housing or multiple sides, such as the top, right side and left side, of the housing 510. The housing 510 may have a plurality of feet or legs 540 attached to the bottom of the housing. The bottom 516 of the housing 510 may have a plurality of vents 518 for venting from the interior of the gas-enhanced generator.

On the face 512 of the housing 514 there is a touchscreen display 520 and a plurality of connectors 532, 534 for connecting various accessories to the generator, such as an argon plasma probe, a hybrid plasma probe, a cold atmospheric plasma probe, or any other electrosurgical attachment. There is a gas connector 536 for connecting, for example, a $CO_2$ supply for insufflating an abdomen. The face 512 of the housing 510 is at an angle other than 90 degrees with respect to the top and bottom of the housing 510 to provide for easier viewing and use of the touch screen display 520 by a user.

One or more of the gas control modules may be mounting within a gas-enhanced electrosurgical generator 500. A gas pressure control system 200 for controlling a plurality of gas control modules 220, 230, 240 within a gas-enhanced electrosurgical generator is described with reference to FIGS. 2A-2D. A plurality of gas supplies 222, 232, 242 are connected to the gas pressure control system 200, and more specifically, to the respective gas control modules 220, 230, 240 within the gas pressure control system 200. The gas pressure control system 200 has a power supply 202 for supplying power to the various components of the system. A CPU 210 controls the gas pressure control modules 220, 230, 240 in accordance with settings or instructions entered into the system through a graphical user interface on the display 120. The system is shown with gas control modules for $CO_2$, argon and helium, but the system is not limited to those particular gases. In the embodiment shown in FIGS. 2A-2D, the $CO_2$ is shown as the gas used to insufflate an abdomen (or other area of a patient). The gas pressure control system 200 has a 3-way proportional valve connected to the gas control module 220. While FIG. 2A shows the 3-way proportional valve connected only to the CO2 control module 220, the 3-way proportional valves could be connected to a different gas control module 230 or 240. The gas pressure control system 200 further has an HF power module 250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. Nos. 4,040,426 and 4,781,175. The system further could have a converter unit for converting the HF power to a lower frequency, such as may be used for cold atmospheric plasma and is described in U.S. Patent Application Publication No. 2015/0342663. As used herein, the term "high frequency" means a frequency above 300 Hz and "low frequency" means a frequency less than 300 Hz.

The outlet port of gas control module 220 is connected to a connector 136 on the generator housing. While connector 136 and the other connectors are shown on the front face of the housing 110, they could be elsewhere on the housing. The outlet ports of gas control modules 230, 240 each are connected to tubing or another channel to a connector 132. A connector 152 connects to connector 136 and is as tubing that runs to and connects to tubing 292. The tubing 292 is connected to a pressure control valve or stopcock 280 and extends into the trocar. The pressure control valve 280 is used to control pressure within the patient. The gas pressure control system further has a pressure sensor 282 connected to the tubing 292 to sense pressure in the tubing 292 and a pressure sensor 284 for sensing pressure in the pressure control valve 280. As shown in FIG. 2C, the tubing 292 is a tube within a tube such that gas supplied from the generator travels to the trocar and patient through tube 296 and gas is released out of the patient through tube 294.

Figure 6A:
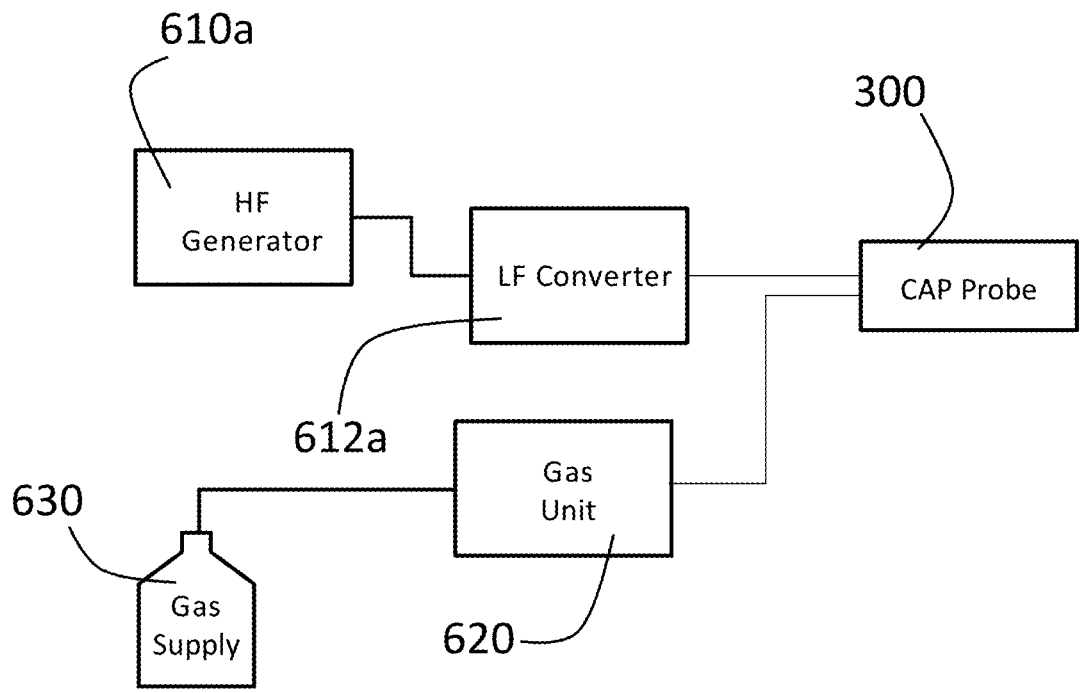
FIG. 6A is a block diagram of a preferred embodiment of a gas-enhanced electrosurgical generator in accordance with the present invention configured to perform an argon-enhanced electrosurgical procedure.
Figure 6B:
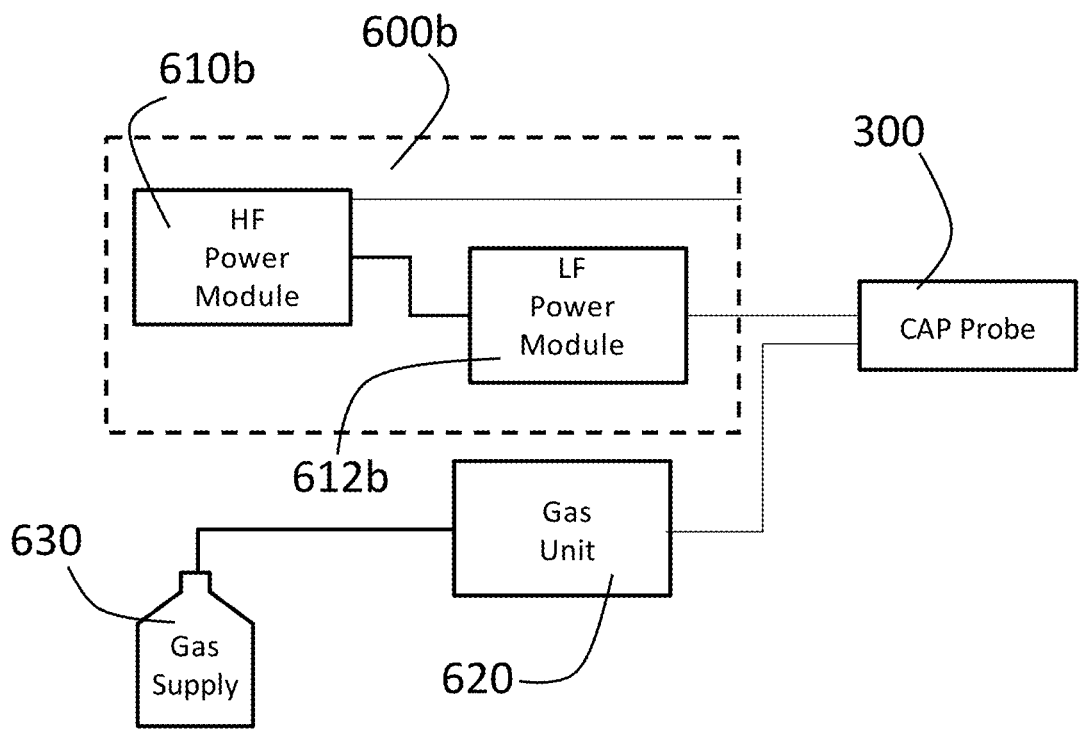
FIG. 6B is a block diagram of a preferred embodiment of a gas-enhanced electrosurgical generator in accordance with the present invention configured to perform a cold atmospheric plasma procedure.
Figure 6C:
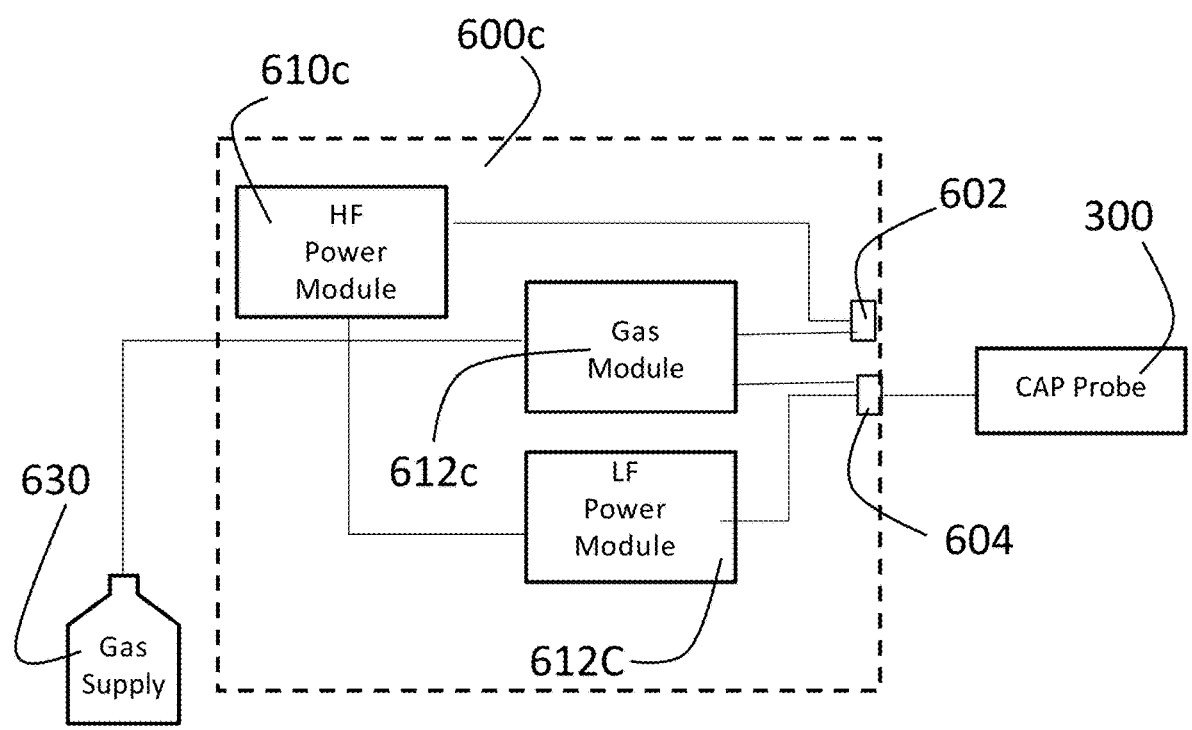
FIG. 6C is a block diagram of a preferred embodiment of a gas-enhanced electrosurgical generator in accordance with the present invention configured to perform a cold atmospheric plasma procedure.

FIGS. 6A-6C show alternative embodiments of a system for producing cold plasma. In FIG. 6A, a conventional high frequency (HF) generator 610a supplies HF power to a low frequency (LF) converter than down converts the frequency of the energy. A gas such as helium is supplied from a gas supply 630 to a gas unit 620. The low frequency energy and helium gas are then supplied to a CAP accessory or probe 300. In an alternative embodiment shown in FIG. 6B, a CAP generator has a high frequency power module 610b and a low frequency power module 612b. The low frequency power module down converts the frequency of energy form the high frequency power module 610b to produce a low frequency signal. A gas such as helium is supplied from a gas supply 630 to a gas unit or module 620. The low frequency energy and helium gas are then supplied to a CAP accessory or probe 300. As shown in FIG. 6C, in another alternative embodiment an integrated gas-assisted CAP and HF generator is shown. The integrated generator has a high frequency power module 610c, a low frequency power module 612c, and a gas module 620c. The generator further has connectors 602 and 604 for connecting the gas module and power supplies to an accessory or probe 300.

A gas pressure control system 200 for controlling a plurality of gas control modules 220, 230, 240 within a gas-enhanced electrosurgical generator is described with reference to FIGS. 6C-6D. A plurality of gas supplies 222, 232, 242 are connected to the gas pressure control system 200, and more specifically, to the respective gas control modules 220, 230, 240 within the gas pressure control system 200. The gas pressure control system 200 has a power supply 202 for supplying power to the various components of the system. A CPU 210 controls the gas pressure control modules 220, 230, 240 in accordance with settings or instructions entered into the system through a graphical user interface on the display 120. The system is shown with gas control modules for $CO_2$, argon and helium, but the system is not limited to those particular gases. In the embodiment shown in FIGS. 6C-6D, the $CO_2$ is shown as the gas used to insufflate an abdomen (or other area of a patient). The gas pressure control system 200 has a 3-way proportional valve connected to the gas control module 220. While FIG. 6C shows the 3-way proportional valve connected only to the CO2 control module 220, the 3-way proportional valves could be connected to a different gas control module 230 or 240. The gas pressure control system 200 further has an HF power module 250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. Nos. 4,040,426 and 4,781,175. The system further could have a converter unit for converting the HF power to a lower frequency, such as may be used for cold atmospheric plasma and is described in U.S. Patent Application Publication No. 2015/0342663.

Figure 6D:
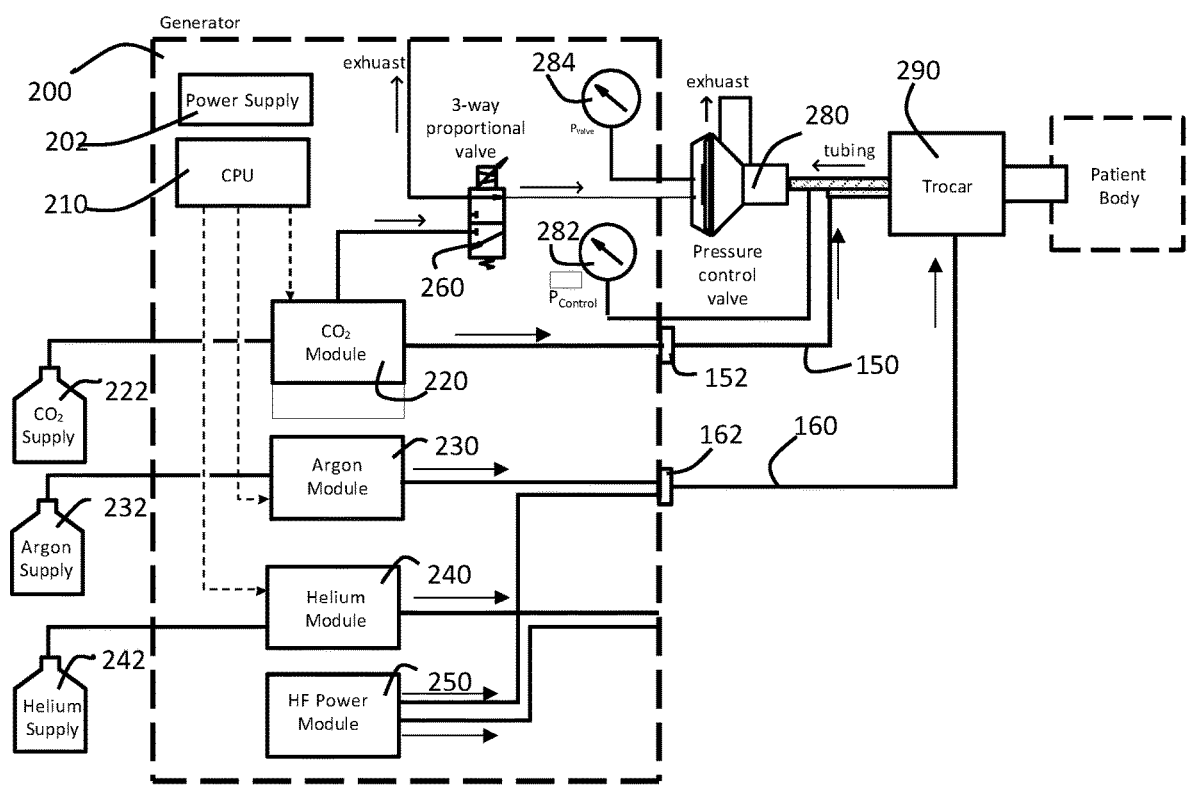
FIG. 6D is a block diagram of a preferred embodiment of a gas-enhanced electrosurgical generator having a pressure control system in accordance with the present invention configured to perform an argon-enhanced electrosurgical procedure.
Figure 6E:
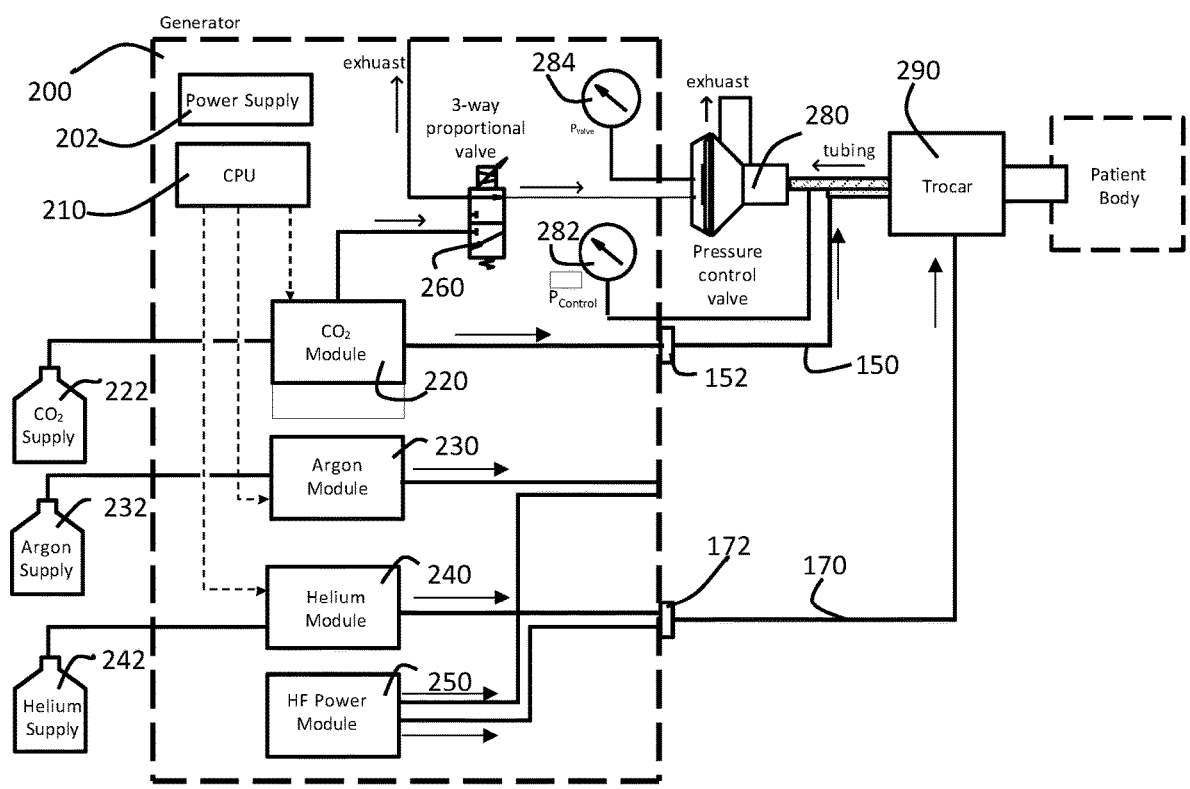
FIG. 6E is a block diagram of a preferred embodiment of a gas-enhanced electrosurgical generator having a pressure control system in accordance with the present invention configured to perform a cold atmospheric plasma procedure.

An alternative embodiment of the gas pressure control system is shown in FIG. 6D. This this system the automatic stopcock or pressure control valve 280 has been replaced by a manual relief valve 280a that is controlled or operated by the surgeon using the system.

A gas control module 700 in accordance with the present invention is designed for gas-enhanced electrosurgical systems. Conventionally, gas-enhanced electrosurgical systems have an electrosurgical generator and a gas control unit that have separate housings. The conventional gas control unit typically controls only a single gas such as argon, $CO_2$ or helium. The present invention is a gas control module 700 that may be used in a gas control unit or in a combined unit functioning both as an electrosurgical generator and as a gas control unit. Further, a plurality of gas control modules in accordance with the present invention may be combined in a single gas control unit or combination generator/gas control unit to provide control of multiple gases and provide control for multiple types of gas-enhanced surgery such as argon gas coagulation, hybrid plasma electrosurgical systems and cold atmospheric plasma systems.

Figure 7A:
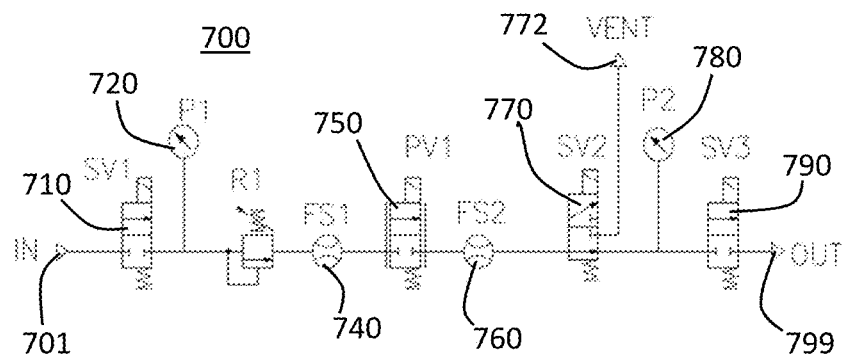
FIG. 7A is a schematic flow diagram illustrating the gas flow through the module and the method by which the module controls the gas flow in accordance with a preferred embodiment of the present invention.

FIG. 7A is a schematic flow diagram illustrating the gas flow through the gas control module 700 and the method by which the module 700 controls the gas flow in accordance with a preferred embodiment of the present invention. As shown in FIG. 7A, the gas enters the gas control module at an inlet port (IN) 701 and proceeds to first solenoid valve (SV1) 710, which is an on/off valve. In an exemplary embodiment, the gas enters the gas module at a pressure of 75 psi. The gas then proceeds to a first pressure sensor (P1) 720, to a first pressure regulator (R1) 730. In an exemplary embodiment, the first pressure regulator (R1) 730 reduces the pressor of the gas from 75 psi to 18 psi. After the pressure regulator (R1) 730, the gas proceeds to flow sensor (FS1) 740, which sense the flow rate of the gas. Next, the gas proceeds to proportional valve (PV1) 750, which permits adjustment of a percentage of the opening in the valve. The gas then proceeds to a second flow sensor (FS2) 760, which senses the flow rate of the gas. This second flow sensor (FS2) 760 provides redundancy and thus provides greater safety and accuracy in the system. Next the gas proceeds to a second solenoid valve (SV2) 770, which is a three-way valve that provides for a vent function that can allow gas to exit the module through a vent 772. The gas then proceeds to a second pressure sensor (P2) 780, which provides a redundant pressure sensing function that against produces greater safety and accuracy of the system. Finally, the gas proceeds to a third solenoid valve (SV3) 790, which is a two-way on/off valve that is normally closed and is the final output valve in the module. The gas exits the module at and output port (OUT) 799, which is connected to tubing or other channel that provides a passageway for the gas to flow to an accessory connected to the electrosurgical unit.

Figure 7B:
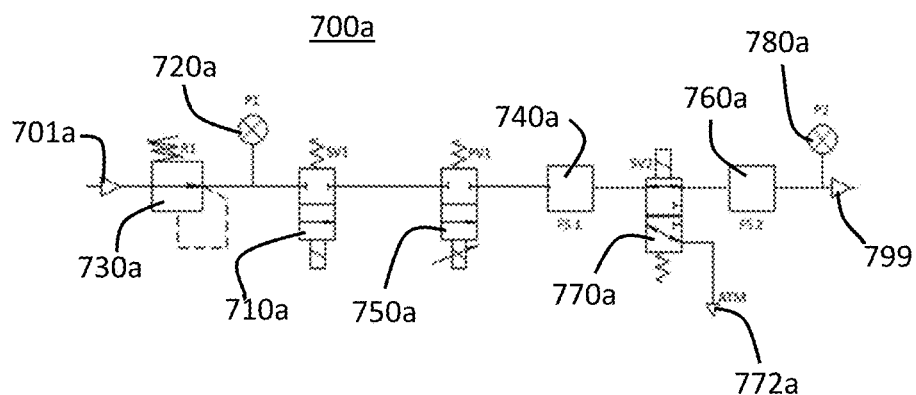
FIG. 7B is a schematic flow diagram illustrating the gas flow through an alternate embodiment of the module and the method by which the module controls the gas flow in accordance with a preferred embodiment of the present invention.

FIG. 7B is a schematic flow diagram of an alternate embodiment of a gas control module illustrating the gas flow through the gas control module 700a and the method by which the module 700a controls the gas flow in accordance with a preferred embodiment of the present invention. As shown in FIG. 7B, the gas enters the gas control module at an inlet port 701a and proceeds to a first pressure regulator (R1) 730a. In an exemplary embodiment, the first pressure regulator (R1) 730a reduces the pressor of the gas from about 50-100 psi to 15-25 psi. After the pressure regulator (R1) 730a, the gas proceeds to a first pressure sensor (P1) 720a and then to a first solenoid valve (SV1) 710a, which is an on/off valve. Next, the gas proceeds to proportional valve (PV1) 750a, which permits adjustment of a percentage of the opening in the valve. Next, the gas proceeds to flow sensor (FS1) 740a, which sense the flow rate of the gas. ext the gas proceeds to a second solenoid valve (SV2) 770a, which is a three-way valve that provides for a vent function that can allow gas to exit the module through a vent 772a. The gas then proceeds to a second flow sensor (FS2) 760a, which senses the flow rate of the gas. This second flow sensor (FS2) 760a provides redundancy and thus provides greater safety and accuracy in the system. The gas then proceeds to a second pressure sensor (P2) 780a, which provides a redundant pressure sensing function that against produces greater safety and accuracy of the system. The gas exits the module at and output port 799a, which is connected to tubing or other channel that provides a passageway for the gas to flow to an accessory connected to the electrosurgical unit.

The various valves and sensors in either embodiment of the module are electrically connected to a main PCB Board through a connector 490. The PCB connector 490 is connected to a PCB Board that has a microcontroller (such as CPU 210 in the embodiment shown in FIG. 2A). As previously noted, a plurality of gas modules can be in a single gas control unit or single electrosurgical generator to provide control of multiple differing gases. The plurality of gas control modules further may be connected to the same PCB Board, thus providing common control of the modules.

Figure 8:
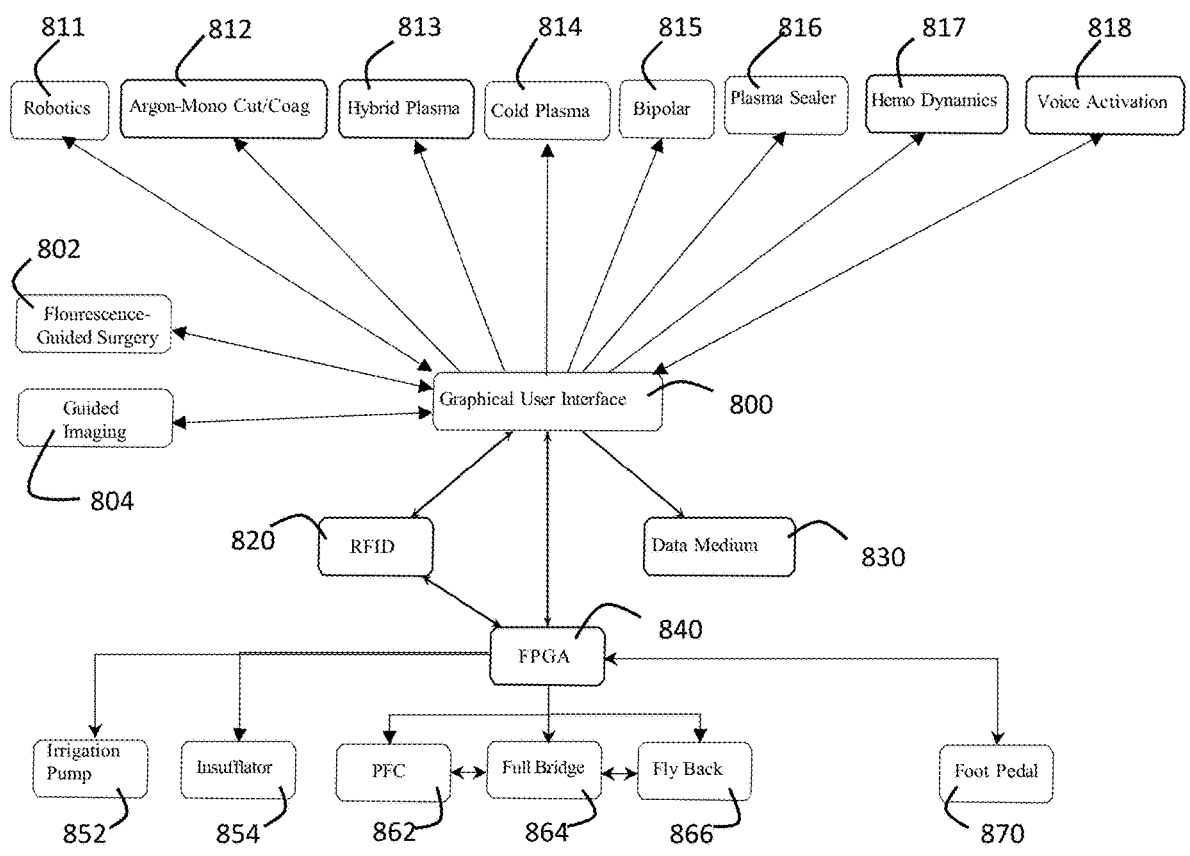
FIG. 8 is a diagram of a graphical user interface in accordance with a preferred embodiment of the present invention.

As shown in FIG. 8, the generator further may have graphical user interface 800 for controlling the components of the system using the touch screen display 520. The graphical user interface 500 for example, may control robotics 811, argon-monopolar cut/coag 812, hybrid plasma cut 813, cold atmospheric plasma 814, bipolar 815, plasma sealer 816, hemo dynamics 817 or voice activation 818. The graphical user interface further may be used with fluorescence-guided surgery 802. For example, J. Elliott, et al., "Review of fluorescence guided surgery visualization and overlay techniques," BIOMEDICAL OPTICS EXPRESS 3765 (2015), outlines five practical suggestions for display orientation, color map, transparency/alpha function, dynamic range compression and color perception check. Another example of a discussion of fluorescence-guided surgery is K. Tipirneni, et al., "Oncologic Procedures Amenable to Fluorescence-guided Surgery," Annals of Surgery, Vo. 266, No. 1, July 2017). The graphical user interface (GUI) further may be used with guided imaging such as CT, MIll or ultrasound. The graphical user interface may communicate with RFID 820 (such as may be found in various electrosurgical attachments) and may collect and store usage data in a storage medium 830. The graphical user interface 800 communicates with FPGA 840, which may control irrigation pump 852, insufflator 854, PFC 862, full bridge 864 for adjusting the power output, fly back 866 for regulating the power (DC to AC) and a foot pedal 870. The GUI 800 further communicates with a database of cancer cell line data with associated predicted CAP settings or dosages via a CPU in the generator.

Figure 9:
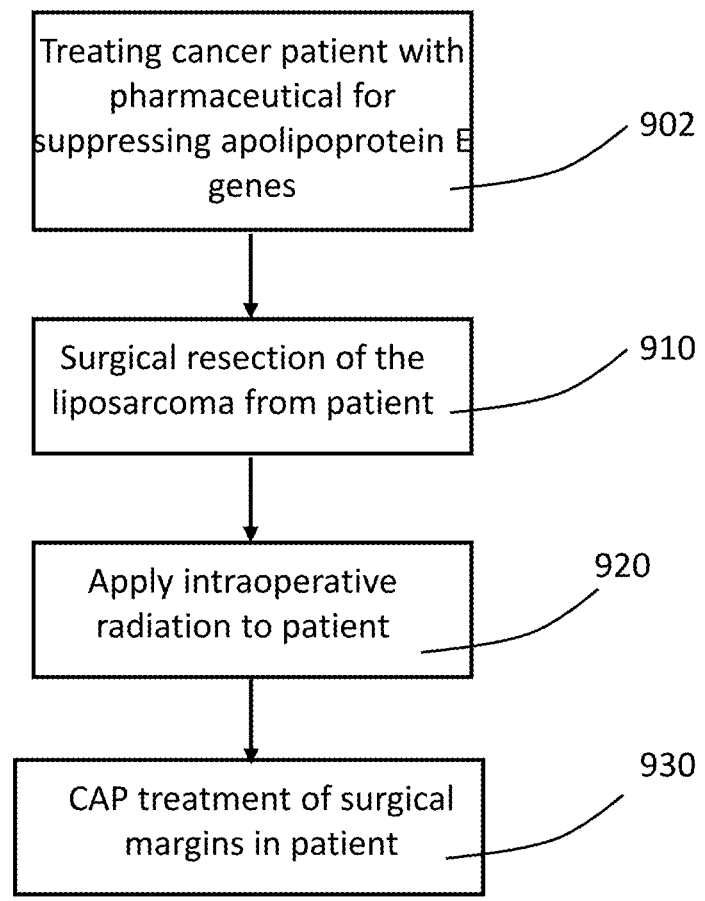
FIG. 9 is a flow chart of a method for performing CAP treatment in accordance with a preferred embodiment of the present invention.

Experiments:

FIG. 9 illustrates a method with which a patient was treated. A cancer patient is treated with a pharmaceutical for suppressing the apolipoprotein E gene 902. The liposarcoma in the patient is surgically resected 910. Intraoperative radiation treatment is applied to the patient 920. CAP treatment is then performed on the surgical margins where the liposarcoma was surgically resected from the patient 930.

Figure 10:
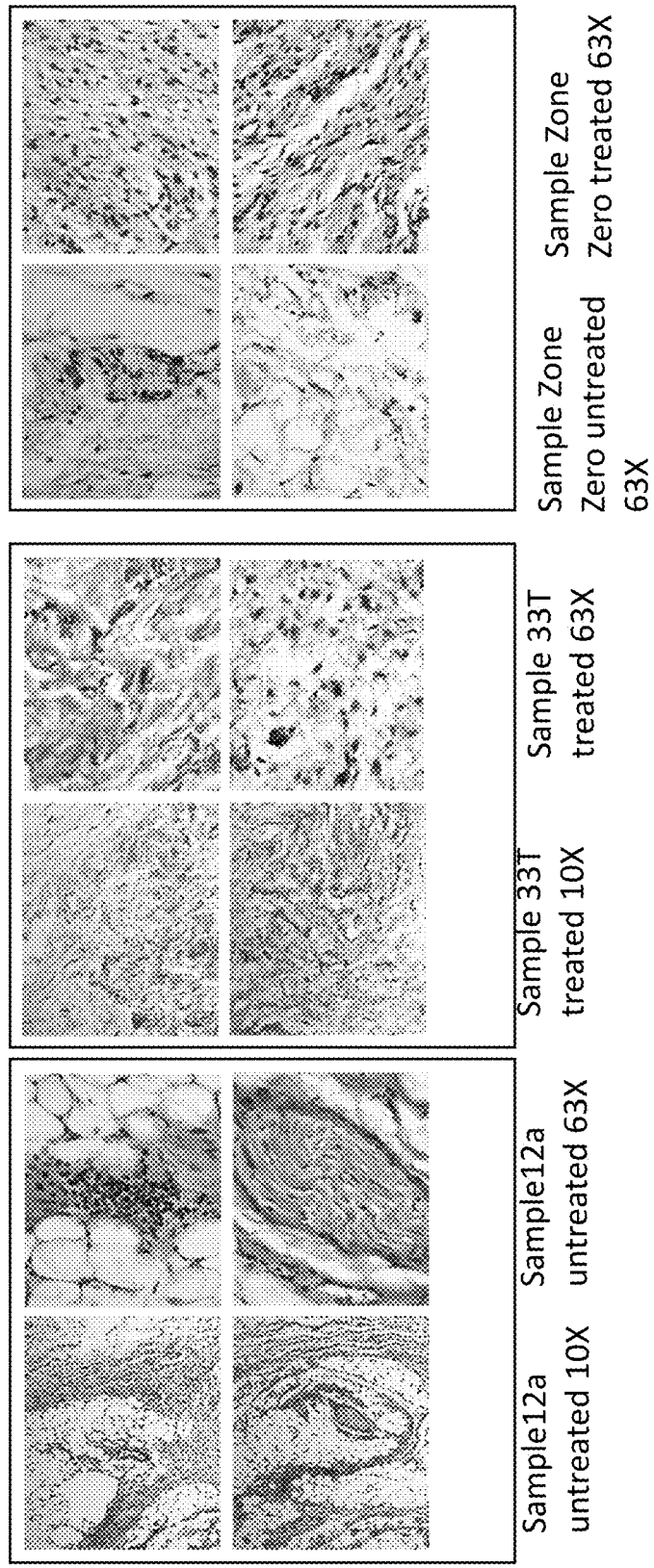
FIG. 10 is a group of histology slides of untreated myxofibrosarcoma and CAP-treated tissues under CAP treatment conditions: 25V 5 min.
Figure 11:
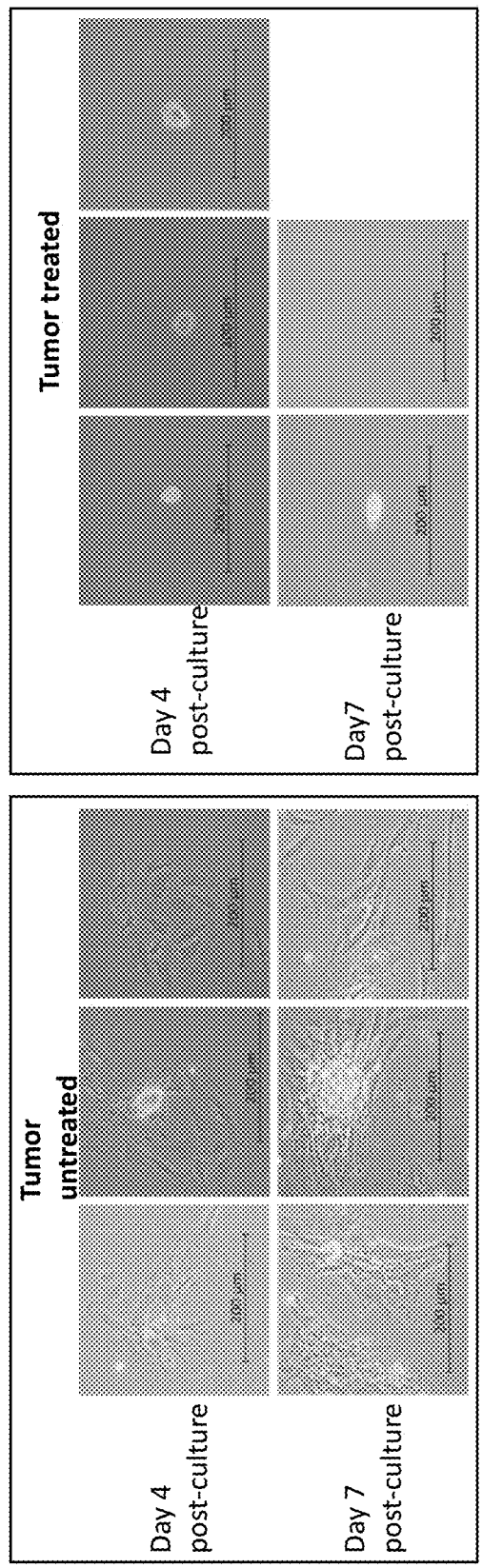
FIG. 11 is 2D primary culture slides from the untreated myxofibrosarcoma and CAP-treated tumor tissues on day 4 and day 7 after treatment. CAP treatment conditions: 25V 5 min.

FIG. 10 is a group of histology slides of untreated myxofibrosarcoma and CAP-treated tissues. CAP treatment conditions: 25V 5 min. The images show lipoblasts and capillaries in a predominantly stroma in CAP untreated tissue sections and collagenous structure predominately visible in treated tissue sections FIG. 11 is a series of images of 2D primary culture slides from the untreated myxofibrosarcoma and CAP-treated tumor tissues on day 4 and day 7 after treatment. CAP treatment conditions: 25V 5 min.

Large heterogenous population of primary cells from the untreated myxofibrosarcoma tissues were adherent and proliferated over time.

Few primary cells from the CAP-treated myxofibrosarcoma tissues were adherent and dormient but did not survive for more than 7 days.

Figure 12:
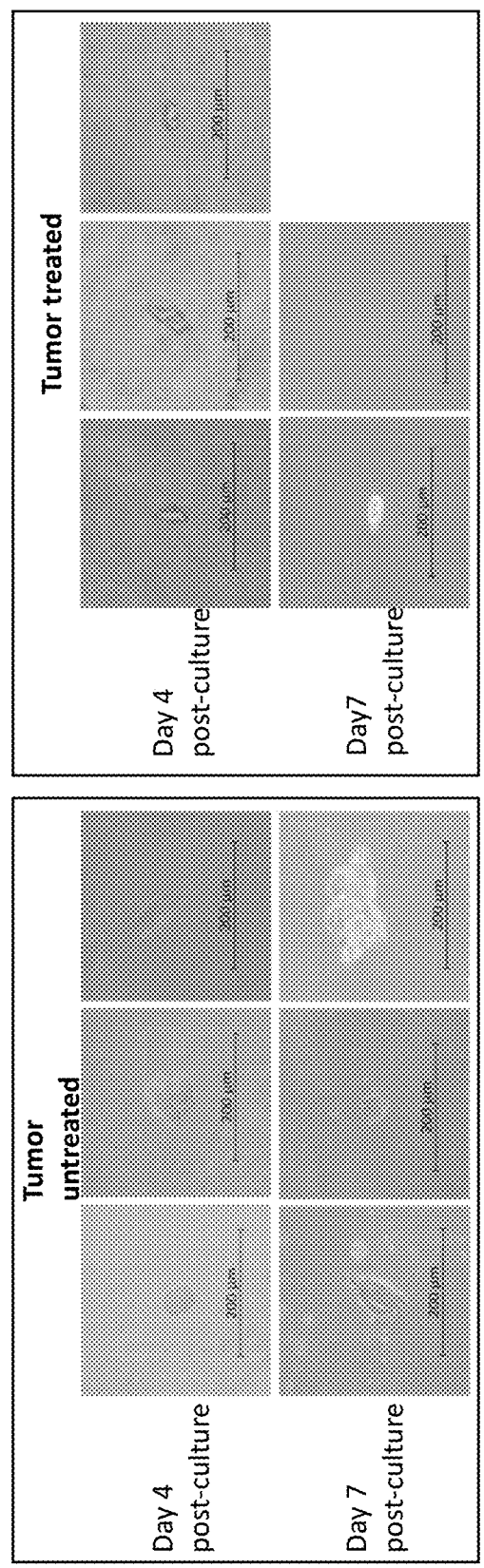
FIG. 12 illustrates organoid cultures from the untreated myxofibrosarcoma and CAP-treated tumor tissues: Day 4 and Day 7.

FIG. 12 illustrates organoid cultures from the untreated myxofibrosarcoma and CAP-treated tumor tissues: Day 4 and Day 7. CAP treatment conditions: 25V 5 min Several biocysts from the untreated myxofibrosarcoma tissues formed organoids with smooth external morphology. Few biocysts from the CAP-treated myxofibrosarcoma tissues formed rough morphology and fragmented over time.

Figure 13:
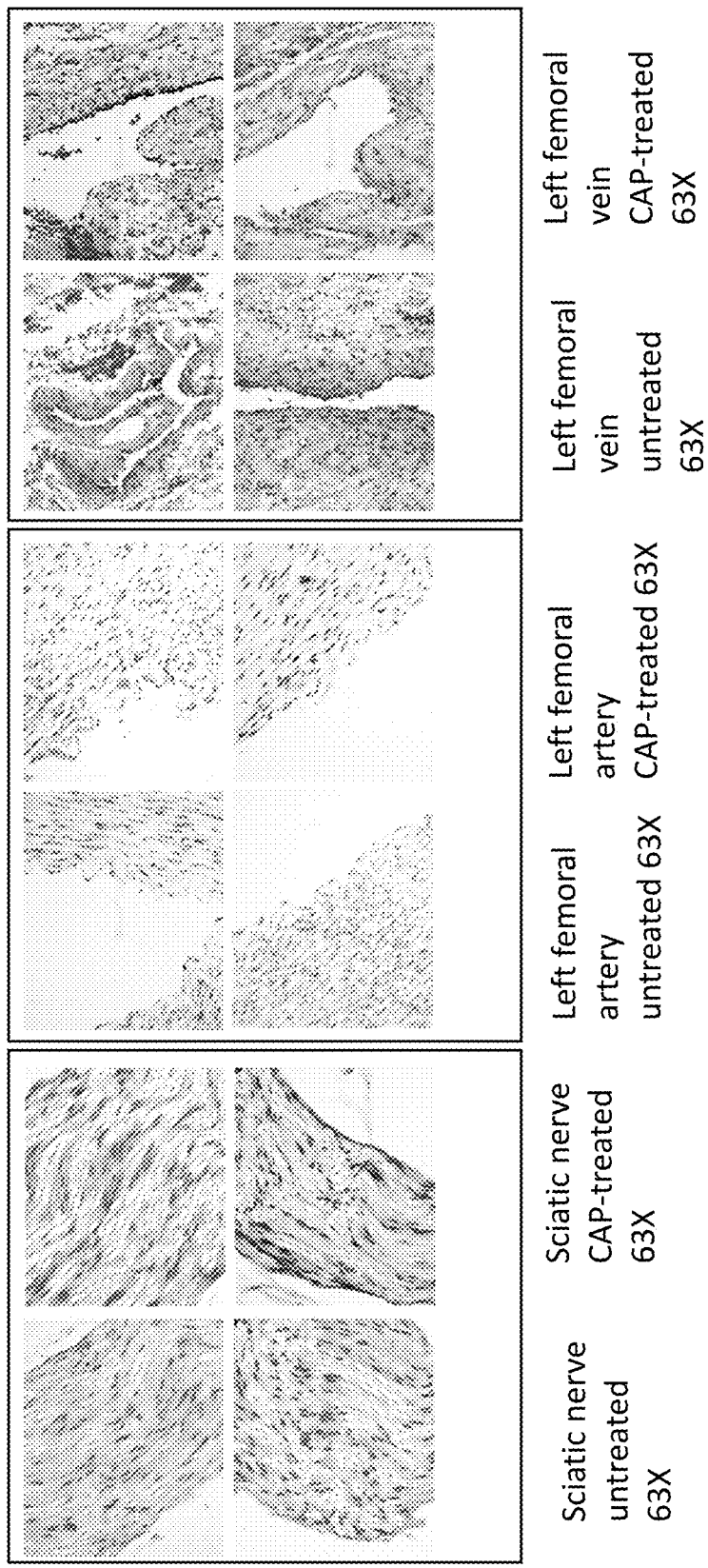
FIG. 13 is a group of histology slides of CAP treatment on porcine sciatic nerve, left femoral vein and left femoral artery.

FIG. 13 illustrates histology slides of untreated and CAP-treated porcine tissues. CAP treatment conditions: 40V 2.5 min. No histological changes between the untreated and CAP-treated tissues were observed The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for treating cancer comprising:
   treating a patient with a pharmaceutical for suppressing apolipoprotein E genes;
   surgically resecting a liposarcoma from the patient; and
   performing cold atmospheric plasma treatment on surgical margins of an area in the patient where the liposarcoma was resected after said patient is treated with the pharmaceutical for suppressing the apolipoprotein E genes.

2. A method for treating cancer according to claim 1 further comprising:
   performing intraoperative radiation treatment on the patient during the surgical resection of the liposarcoma from the patent.

3. A method for treating cancer according to claim 1 wherein the cold atmospheric plasma treatment is performed for at least 7 minutes.

4. A method for treating cancer according to claim 3 wherein the cold atmospheric plasma treatment is performed for at least 7 minutes at a power setting of 120 W.

5. A method for applying cold atmospheric plasma treatment to target tissue comprising the steps of:
   treating a patient with a pharmaceutical for suppressing apolipoprotein E genes;
   surgically resecting a liposarcoma from the patient; and
   after said patient is treated with the pharmaceutical for suppressing the apolipoprotein E genes, performing the following steps:
      selecting through a graphical user interface a particular liposarcoma cell line associated with target tissue;
      retrieving, with a computing device, settings data associated with said selected liposarcoma cell line from a database of cell line data and associated settings data in a storage;
      applying, with said computing device, said retrieved settings data to a cold atmospheric plasma system; and
   performing cold atmospheric plasma treatment on surgical margins of an area in the patient where the liposarcoma was resected.

* * * * *